US010537501B2

(12) United States Patent
Kim et al.

(10) Patent No.: US 10,537,501 B2
(45) Date of Patent: *Jan. 21, 2020

(54) URETHANE FOAM FOR USE IN IMPREGNATING COSMETIC COMPOSITION

(71) Applicant: AMOREPACIFIC CORPORATION, Seoul (KR)

(72) Inventors: Kyung Nam Kim, Yongin-si (KR); Jung Sun Choi, Yongin-si (KR); Min Kyung Shim, Yongin-si (KR); Kyung Ho Choi, Yongin-si (KR); Yeong Jin Choi, Yongin-si (KR)

(73) Assignee: Amorepacific Corporation, Seoul (KR)

(*) Notice: Subject to any disclaimer, the term of this patent is extended or adjusted under 35 U.S.C. 154(b) by 0 days.

This patent is subject to a terminal disclaimer.

(21) Appl. No.: 16/221,583

(22) Filed: Dec. 17, 2018

(65) Prior Publication Data

US 2019/0117524 A1 Apr. 25, 2019

Related U.S. Application Data

(63) Continuation of application No. 14/034,650, filed on Sep. 24, 2013, which is a continuation-in-part of application No. PCT/KR2012/002141, filed on Mar. 23, 2012.

(30) Foreign Application Priority Data

Mar. 24, 2011 (KR) .................. 10-2011-0026466

(51) Int. Cl.
| | | |
|---|---|---|
| *A61K 8/02* | (2006.01) | |
| *A61K 8/87* | (2006.01) | |
| *A61Q 1/00* | (2006.01) | |
| *A61Q 1/02* | (2006.01) | |
| *A61Q 1/04* | (2006.01) | |
| *A61Q 1/06* | (2006.01) | |
| *A61Q 1/08* | (2006.01) | |
| *A61Q 1/10* | (2006.01) | |
| *A61Q 17/04* | (2006.01) | |
| *C08L 75/06* | (2006.01) | |
| *C08L 75/08* | (2006.01) | |
| *C08G 101/00* | (2006.01) | |

(52) U.S. Cl.
CPC .......... *A61K 8/0216* (2013.01); *A61K 8/0208* (2013.01); *A61K 8/87* (2013.01); *A61Q 1/00* (2013.01); *A61Q 1/02* (2013.01); *A61Q 1/04* (2013.01); *A61Q 1/06* (2013.01); *A61Q 1/08* (2013.01); *A61Q 1/10* (2013.01); *A61Q 17/04* (2013.01); *C08L 75/06* (2013.01); *C08L 75/08* (2013.01); *C08G 2101/00* (2013.01)

(58) Field of Classification Search
CPC ...... A61K 8/0216; A61K 8/0208; A61K 8/87; A61Q 1/00; A61Q 1/04; A61Q 1/06; A61Q 1/08; A61Q 1/10; A61Q 1/02; A61Q 17/04; C08L 75/06; C08L 75/08; C08G 2101/00

See application file for complete search history.

(56) References Cited

U.S. PATENT DOCUMENTS

| | | |
|---|---|---|
| 1,851,462 A | 10/1932 | Steller |
| 2,764,565 A | 9/1956 | Hoppe et al. |
| 3,133,309 A | 5/1964 | Miles |
| 3,463,745 A | 8/1969 | Hofrichter et al. |
| 3,465,759 A | 9/1969 | Haefele |
| 3,748,288 A | 7/1973 | Winkler et al. |
| 4,130,121 A | 12/1978 | Wetzel |
| 4,259,452 A | 3/1981 | Yukuta et al. |
| 4,309,509 A | 1/1982 | Wood |
| 4,323,656 A | 4/1982 | Strickman et al. |
| 4,344,930 A | 8/1982 | MacRae et al. |
| 4,374,935 A | 2/1983 | Decker et al. |
| 4,427,798 A | 1/1984 | Konig et al. |
| 4,440,181 A | 4/1984 | Scherer |
| 4,537,912 A | 8/1985 | Griswold |
| 4,594,835 A | 6/1986 | Gray |
| 4,656,196 A | 4/1987 | Kelly et al. |
| 4,706,693 A | 11/1987 | Spector |
| 4,806,572 A | 2/1989 | Kellett |
| 4,985,467 A | 1/1991 | Kelly et al. |
| 5,064,653 A | 11/1991 | Sessions et al. |
| 5,065,752 A | 11/1991 | Sessions et al. |
| 5,098,621 A | 3/1992 | Hermann |
| 5,296,518 A | 3/1994 | Grasel et al. |
| 5,552,449 A | 9/1996 | Sollers et al. |
| 5,591,779 A | 1/1997 | Bleys et al. |
| 5,961,961 A | 10/1999 | Dobkowski et al. |

(Continued)

FOREIGN PATENT DOCUMENTS

| | | |
|---|---|---|
| BE | 875638 | 8/1979 |
| DE | 2356460 | 5/1974 |

(Continued)

OTHER PUBLICATIONS

"100% Open Cell Flexible Polyurethane Foams", FXI Reticulated Foams, Product Sheet, FXI, Inc., Retrieved from the Internet Nov. 22, 2016, 1 page, <URL: fxi.com>.

(Continued)

*Primary Examiner* — Hasan S Ahmed
(74) *Attorney, Agent, or Firm* — Rothwell, Figg, Ernst & Manbeck, P.C.

(57) ABSTRACT

Provided is a polyether-based urethane foam for impregnating a cosmetic composition. The polyether-based urethane foam has excellent touch feel, portability and stability.

4 Claims, 5 Drawing Sheets

(56) References Cited

U.S. PATENT DOCUMENTS

| | | | |
|---|---|---|---|
| 6,271,277 | B1 | 8/2001 | Bleys et al. |
| 6,391,233 | B1 | 5/2002 | Otani et al. |
| 6,638,986 | B2 | 10/2003 | Falke et al. |
| 6,706,775 | B2 | 3/2004 | Hermann et al. |
| 7,427,412 | B1 | 9/2008 | Painter et al. |
| 7,612,160 | B2 | 11/2009 | Nguyen-Kim et al. |
| 8,784,854 | B2 | 7/2014 | Choi et al. |
| 9,532,637 | B2 | 1/2017 | Choi et al. |
| 2002/0182245 | A1 | 12/2002 | Thomson |
| 2004/0170670 | A1 | 9/2004 | Smith et al. |
| 2005/0159500 | A1 | 7/2005 | Dreier et al. |
| 2006/0235100 | A1 | 10/2006 | Kaushiva et al. |
| 2007/0189975 | A1 | 8/2007 | Thomson |
| 2009/0047495 | A1 | 2/2009 | Hubbs |
| 2011/0014254 | A1 | 1/2011 | Choi et al. |
| 2014/0023689 | A1 | 1/2014 | Kim et al. |
| 2015/0196468 | A1 | 7/2015 | Kim et al. |

FOREIGN PATENT DOCUMENTS

| | | |
|---|---|---|
| EP | 0528705 | 9/2000 |
| GB | 1498363 | 1/1978 |
| JP | 08325125 A | 12/1996 |
| JP | 3015878 B2 | 3/2000 |
| JP | 2002-53640 A | 2/2002 |
| JP | 2003012457 A | 1/2003 |
| JP | 2004267277 A | 9/2004 |
| JP | 2005-152186 A | 6/2005 |
| JP | 2006241150 A | 9/2006 |
| JP | 2007330771 A | 12/2007 |
| JP | 2010-6294 A | 1/2010 |
| JP | 4588357 B2 | 12/2010 |
| KR | 0131075 | 11/1997 |
| KR | 100498655 B1 | 7/2005 |
| KR | 1020090100643 A | 9/2009 |
| KR | 1020130116044 A | 10/2013 |
| KR | 1020140038880 A | 3/2014 |
| KR | 1020150063196 A | 6/2015 |
| WO | 9947127 A1 | 9/1999 |
| WO | 2008112139 | 9/2008 |
| WO | 2009116817 A2 | 9/2009 |
| WO | 2012128589 A2 | 9/2012 |

OTHER PUBLICATIONS

"BB Cushion Sponge is Melting", Posted on the Internet Feb. 4, 2015, <URL: http://www.todayhumor.co.kr/board/view.php?table=fashion&no=142195>.

"Filters for Fishkeeping", EMW filtertechnik, Product Brochure, Retrieved from the Internet Nov. 22, 2016, pp. 1-4, <URL: www.emw.de>.

"Nature Republic CC Cushion Pact Sponge Gets Melted!!", Posted on the Internet Feb. 5, 2015, <URL: http://blog.naver.com/clawsome/220263606984>.

"Reticulated (Open-Cell) & Non-Reticulated (Closed-Cell) Foam Swabs", Berkshire, Retrieved from the Internet Nov. 11, 2016, pp. 1-5, <URL: http://www.berkshire.com/shop/cleanroomcleaningswabs/foam.html>.

"Reticulated Foam" and "Open Cell Polyurethane Foam", Foam Engineers Limited, Retrieved from the Internet Jul. 8, 2016, pp. 1-2, <URL: http://www.foamengineers.co.uk/foammanufacturingsuppliers/reticulated-foam>.

"Reticulated Foam-Polyurethane-based foam with open cellular structure", material sample shop.com, Retrieved from the Internet Jul. 8, 2016, pp. 1-2, <URL: https://www.materialsampleshop.com/products/reticulatedfoampolyurethane-based-foam-with-open-cellular-structure>.

"Reticulated Open Cell Black Packaging Foam with Polyester Polyurethaner Material", Changzhou Dayetengfei Sponge Factory, Retrieved from the Internet Jul. 8, 2016, pp. 1-3, <URL: http://www.customizedfoam.com/sale-7566632-reticulatedopen-cellblack-packaging-foam-with-polyesterpolyurethaner-material.html>.

"Reticulated Polyurethane Foam", FXI Innovations, Retrieved from the Internet Nov. 11, 2016, pp. 1-3, <URL: http://fxi.com/foamtechnologies/processes/reticulation.php>.

"Reticulated Polyurethane Foam", UFP Technologies, Retrieved from the Internet Jul. 8, 2016, pp. 1-3, <URL: http://www.ufpt.com/materials/foam/reticulatedpolyurethane-foam.html>.

"Reticulated Polyurethane Foam: Quenching vs. Zapping", UFP Technologies, Retrieved from the Internet May 12, 2016, <URL: http://www.ufpt.com/resource-center/quenching-vs-zappingreticulated-polyurethane/>.

"Trend of Global Urethane Raw Materials and Products Market", KIET Overseas Industrial Information, Retrieved from the Internet Nov. 15, 2016, pp. 1-2, <URL: http://www.kiet.go.kr/servlet/isearch?mode=view&dataNo=43619>.

"Optimization Technology Support for Polyurethane Foam Production through Analysis of Correlations Between CellStructure and Properties", Ministry of Commerce, Industry and Energy, Sep. 30, 2003, pp. 8, 11 and 12, KR.

Canadian Office Action for corresponding Canadian Patent Application No. 2,804,298 dated Jan. 18, 2017, citing previously filed reference.

Canadian Office Action for corresponding Canadian Patent Application No. 2,804,298 dated Jan. 4, 2016, citing U.S. Pat. No. 3,133,309 and previously filed references.

Canadian Office Action for corresponding Canadian Patent Application No. 2,804,298 dated Sep. 12, 2016.

Canadian Office Action—Canadia Application No. 2804298 dated May 29, 2014.

Canadian Office Action—Canadia Application No. 2804298 dated Oct. 28, 2013.

Canadian Office Action—Canadian Application No. 2804298 dated May 6, 2015, citing U.S. Pat. No. 3,133,309.

Canadian Protest—Canadia Application No. 2804298 dated Mar. 30, 2015, citing U.S. Pat. No. 3,133,309.

Chang-Seop Oh, "Recent Prospect of Polyurethanes", ReSEAT Analysis Report, Sep. 10, 2004, pp. 1-7, KR.

Chinese Office Action for corresponding Chinese Patent Application No. 201280002267.3 dated Mar. 30, 2016.

Chinese Office Action—Chinese Application No. 201280002267.3 dated Dec. 3, 2014, citing previously filed references CN101977587 and JP4588357.

Chinese Office Action—Chinese Application No. 201280002267.3 dated Mar. 18, 2014, citing previously filed references CN101977587 and US20090047495.

Chinese Office Action—Chinese Application No. 201280002267.3 dated Sep. 8, 2015.

Chinese Patent Invalidation Request for corresponding Chinese Patent Application No. 201280002267.3.

European Office Action for corresponding European Patent Application No. 12759918.1 dated Mar. 1, 2016.

European Office Action—European Application No. 12759918.1 dated Aug. 11, 2015.

European Office Action—European Application No. 12759918.1 dated Jun. 18, 2015, citing U.S. Pat. No. 3,133,309.

European Office Action—European Application No. 12759918.1 dated Oct. 12, 2014.

European Search Report—EP Application No. 12759918.1 dated Jan. 22, 2014 from European Patent Office.

Extract from pp. 22-23 of Korean Patent Court Ruling (case No. 2016heo8667), 1 page.

Foaming Plant, Copyrights 2006, pp. 1-7, Retrieved from the Internet Jun. 25, 2018<URL:http://www.foamtecintl.com/index.php?shpage=vpage&vpage=fpprofile&lang=en&plan=FP>.

George Woods, "Flexible Polyurethane Foams", Chemistry and Technology, 1982, pp. 94-95, Applied Science Publishers Ltd., Essex, England.

Indian Office Action—Indian Application No. 10805/CHENP/2012 dated Jul. 14, 2017, citing references listed within.

INOAC—Reticulated PU Foam, Posted: Nov. 2009, p. 1, Retrieved from the Internet Sep. 2, 2015, <URL: http://www.inostech.com/>.

International Search Report for International Application No. PCT/KR2012/002141 dated Oct. 31, 2012.

(56) References Cited

OTHER PUBLICATIONS

Japanes Office Action—Japan Application No. 2014-008657 dated Jun. 18, 2015.
Japanese Office Action for corresponding Japanese Patent Application No. 2014-008657 dated Mar. 9, 2017, citing previously filed reference.
Japanese Office Action for corresponding Japanese Patent Application No. 2014-008657 dated May 31, 2016, citing previously filed reference.
Japanese Office Action—Japan Application No. 2014-008657 dated Sep. 11, 2015.
Jong-Rae Park, "Catalytic Glycolysis of Polyether Urethane Foam Waste", Master's Thesis, Chonnam National University Graduate School, Department of Chemical Engineering, Aug. 1999, pp. 4-5, KR.
Korean Office Action with English Translation for Application No. 10-2011-0026466 dated Dec. 16, 2012.
Korean Office Action with English Translation for Application No. 10-2011-0026466 dated Jun. 6, 2012.
Malaysian Examination Report—Application No. PI2013000328 dated Apr. 3, 2015, citing previous filed references.
Notice of Allowance with English Translation for Application No. 10-2011-0026466 dated Apr. 17, 2013.
Notice of Opposition for EP 12759918.1 from European Patent Office dated Jul. 19, 2018, citing the above references.
Open Cell Foam, The Foam Factory, Retrieved from the Internet Nov. 11, 2016, pp. 1-2, <URL: http://www.thefoamfactory.com/opencellfoam/filter.html>.
Polyurethane Foam, p. 1, <URL: http://web.archive.org/web/20090220164156/http://casefoam.com/Polyurethane-foam.htm>.
Polyurethane Foam, Retrieved from the Internet Nov. 15, 2016, pp. 1-2, <URL: https://web.archive.org/web/20021223120233/http://www.casefoam.com/Polyurethanefoam.htm>.
Tony Abisaleh et al., "Polyurethane Technology & Applications", 18 pages.
Result report of reproduction experiments on Amorepacific's patent (No. 1257628), dated 2017, 21 pages.
Reticulated foam, Edited on Jun. 3, 2018, pp. 1-3, Retrieved from the Internet Jun. 15, 2018 <URL:https://en.wikipedia.org/wiki/Reticulated_foam>.
"Reticulated Polyurethane Foam", UFP Technologies, Retrieved from the Internet Jul. 8, 2016, pp. 1-3.
Reticulated Foam, Australian Foam Manufacturer, Joyce Foam Products, Retrieved from the Internet Nov. 10, 2016, <URL: http://www.joyce.com.au/foams/reticulatedfoam/>.
Seong-Mi Park, "Report on Stability Test of Sponge Impregnated with LLBB Cushion Cosmetic Composition", Cosmax R&I Institute, Apr. 19, 2017, pp. 1-5, Korea.
Sang-Beom Kim, "About Structure and Properties of Polyurethane Foam", Letter of Opinion, May 9, 2016, pp. 14.
Shimin Wu, et al., "Concise Dictionary of Fine Chemicals", Shenyang: Liaoning Science and Technology, (Jun. 1999), pp. 1-7.
Singaporean Written Opinion—Application No. 201209361-3 dated Sep. 9, 2013, citing previous filed references.
Taiwanese Office Action—TW Application No. 101109975 dated Jan. 13, 2014, citing previous filed references.
Taiwanese Office Action—TW Application No. 101109975 dated Feb. 10, 2014, citing previous filed references.
UFP Technologies—Reticulated Foam, (Copyright 2011), pp. 1-2, Retrieved from the Internet Sep. 2, 2015, <URL: http://www.ufptcom/>.
Written Opinion for International Application No. PCT/KR2012/002141 dated Oct. 31, 2012.
Decision of Intellectual Property Trial and Appeal Board, 6th Department, Trial No. 2018Dang (decision reversing the original decision)76.
Decision of Intellectual Property Trial and Appeal Board, 7th Department, Trial No. 2018Jeong49.
Decision of Patent Court, 1st Dvision, Case No. 2016Heo8667 Invalidation of Registration (Patent).
Decision of Supreme Court, 1st Division, Case No. 2018Hu10596 Invalidation of Registration (Patent).
Kamicokrolock, "Review, Etude house Cushion Foundation", website contents, Mar. 14, 2015, 3 pages.
Merquinsa, Polyurethane Types, Web site contents, pp. 1-8.
Meyer R. Rosen (ed.), Delivery System Handbook for Personal Care and Cosmetic Products, 2005, pp. 513-525.
Michael Szycher, Szycher's Handbook of Polyurethanes, 1999, p. 7-6.
Michael Szycher, Szycher's Handbook of Polyurethanes, 1999, pp. C-8, 21, and 24.
Mihail Ionescu, "Chemistry and Technology of Polyols for Polyurethanes", 2005, pp. 2-4, 49-50, 263, 538-540, 547, Rapra Technology Limited.
Polyurethane Technology & Applications, pp. 107-108.
Polyurethane Technology & Applications, pp. 311-330.
Polyurethane Technology & Applications, pp. 3-5, 89-90, 123, 125, 169-171, 223-226.
Seong-Mi Park, Researcher's Statement, COSMAX R&I Institute, Apr. 17, 2017, 1 page.
T. Thomson, Design and Applications of Hydrophilic Polyurethanes, 2000, pp. 1-9, Preface xi-xiii.
Test Result Sheet, "Stability Test of LLBB Cushion", Korea Conformity Laboratories, 2017, pp. 1-5.
www.ifacemaker.com, a review on ALMAY Nearly Naked Foundation, May 29, 2003.
Alain Parfondry, "Polyurethane Technology & Applications", 15 pages, Nov. 2002.
Declaration of R. Randall Wickett, Petition for Inter Partes Review of U.S. Pat. No. 8,784,854 under U.S.C. §§311-319 and 37 C.F.R. §§42.1-.8, 42.100-,123, Jul. 27, 2018, 90 pages.
The HLB System, a time-saving guide to emulsifier selection, 22 pages, Mar. 1980.
Declaration of Robert Y. Lochhead, Ph.D., FRSC, Case IPR2018-01516, U.S. Pat. No. 8,784,854 B2, dated Nov. 30, 2018, 185 pages.
Petition for Inter Partes Review of U.S. Pat. No. 8,784,854 under U.S.C. §§311-319 and 37 C.F.R. §§42.1-.8, 42.100-.123, dated Aug. 6, 2018, 78 pages.
Patent Owner's Preliminary Response, Case IPR2018-01516, U.S. Pat. No. 8,784,854 B2, dated Nov. 30, 2018, 70 pages.
Decision: Denying Institution of Inter Partes Review 35 U.S.C. § 314(a), Case IPR2018-01516, U.S. Pat. No. 8,784,854 B2, Feb. 20, 2019, 29 pages.

URETHANE FOAM FOR USE IN IMPREGNATING COSMETIC COMPOSITION

CROSS-REFERENCE TO RELATED APPLICATION

This application is a continuation-in-part of U.S. patent application Ser. No. 14/034,650, filed on Sep. 24, 2013, which is a continuation-in-part of International Application No. PCT/KR2012/002141, filed on Mar. 23, 2012, which claims priority to Korean Patent Application No. 10-2011-0026466, filed on Mar. 24, 2011.

TECHNICAL FIELD

This disclosure relates to urethane foam for use in impregnating cosmetic composition.

BACKGROUND ART

In the old days, cosmetic compositions were used mainly indoors. However, as leisure activities have been generalized recently and modern life styles have been changed correspondingly, cosmetic compositions have been frequently used outdoors. Particularly, in the old days, UV protecting cosmetic compositions were used mostly in summer seasons. However, as modern people enjoy outdoor activities and recognize hazard of UV rays more and more, there is a tendency for UV protecting cosmetic compositions to be used frequently throughout all the seasons besides summer seasons. Therefore, there is an increasing need for cosmetic compositions convenient to use and easy to carry.

Polyester-based urethane foam was developed accidentally by a German technical specialist in the late 1940's during which development of plastics was in the midst. Since such urethane foam is based on polyester, it is also called ester foam. Producing such urethane foam requires no advanced technology. Thus, polyester-based urethane foam has been produced generally and used in various industrial fields, particularly those requiring strong tensile force.

However, polyester-based urethane foam tends to be broken easily under a wet environment. In addition, it has a microcellular structure and low air permeability, and thus shows low cushiony feel, softness and flexibility. As a result, polyester-based urethane foam is not suitable for use in impregnating a cosmetic composition, particularly a liquid cosmetic composition. Under these circumstances, there is an imminent need for developing urethane foam suitable for use in impregnating a cosmetic composition.

DISCLOSURE

Technical Problem

This disclosure is directed to providing urethane foam for use in impregnating a cosmetic composition, the urethane foam being capable of maintaining high stability of the cosmetic composition to be impregnated therein and high post-impregnation stability.

Technical Solution

In one general aspect, there is provided polyether-based urethane foam for use in impregnating a cosmetic composition.

Advantageous Effects

The polyether-based urethane foam disclosed herein maintains high stability even after carrying out impregnation with a cosmetic composition, and improves portability and touch feel of a cosmetic composition.

MODE FOR INVENTION

In one aspect, there is provided polyether-based urethane foam for use in impregnating a cosmetic composition. In another aspect, the polyether-based urethane foam may function as a carrier in which a cosmetic composition is supported and retained.

As used herein, the term 'urethane foam' means a foamed and solidified polyurethane resin, and is also referred to as 'foamed urethane'.

In one aspect, the polyether-based urethane foam is more resistant against humidity as compared to polyester-based urethane foam, and thus is not broken easily under a high-humidity condition and shows high stability. In addition, the polyether-based urethane foam has a larger cellular structure than polyester-based urethane foam, and thus has improved air permeability, cushiony feel, softness and flexibility. Further, the polyether-based urethane foam requires reduced cost for production, and thus has higher cost-efficiency than polyester-based urethane foam.

In one aspect, urethane foam may include dry urethane foam or wet urethane foam. Particularly, wet polyether-based urethane foam has the properties as shown in the following Table 1.

TABLE 1

| Item | |
|---|---|
| Pore size | 200 μm |
| Surface Properties | Hydrophilic |
| ASKER DUROMETER HARDNESS Type C hardness | 90 |
| Tensile strength | 15 kgf/cm$^2$ |
| Elongation | 260% |
| Apparent specific gravity (g/cm$^3$) | 0.21 |
| Moisture holding ratio | 420% |

Figure 1:
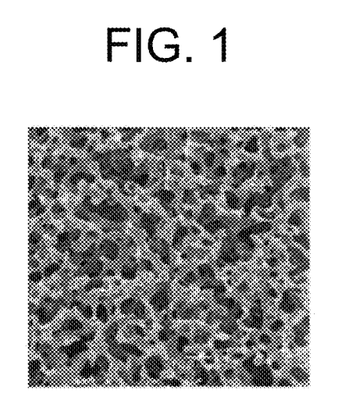
FIG. 1 is a microscopic view of wet polyether-based urethane foam.

In general, wet polyether-based urethane foam has a smaller pore size and more dense structure than dry polyether-based urethane foam. While dry polyether-based urethane foam has oleophilic surface properties, wet polyether-based urethane foam has hydrophilic surface properties as a result of wet foaming. Wet polyether-based urethane foam is continuous microporous urethane foam having uniform and high porosity, shows high water/oil absorbability, and produces no particles spontaneously. FIG. 1 is a microscopic view of wet polyether-based urethane foam.

In one aspect, urethane foam may have a quenched or reticulated structure. In another aspect, urethane foam may have a reticulated structure that allows uniform and easy impregnation with a cosmetic composition and provides a high impregnation ratio.

In one aspect, urethane foam may have a density of 1 to 3 pounds per cubic feet (pcf), particularly 1 to 2 pcf. When urethane foam has a density less than 1 pcf, a cosmetic composition may be liberated excessively and thus is not convenient to use. When urethane foam has a density higher than 3 pcf, it is not possible to provide a sufficient number of pores through which a cosmetic composition is impregnated, thereby making it difficult to impregnate a cosmetic composition effectively.

In one aspect, urethane foam may have a pore number of 70 to 120 pores per inch (ppi), particularly 75 to 95 ppi. When urethane foam has a pore number less than 70 ppi, it has poor elasticity, is not convenient to use and is not amenable to control of the flowability of a cosmetic composition. When urethane foam has a pore number greater than 120 ppi, it provides low durability and poor touch feel of a cosmetic composition during use.

In one aspect, urethane foam may have an ASKER hardness of 10 to 70, particularly 20 to 60, and more particularly 30 to 50 as measured by DUROMETER HARDNESS TESTER (Type F) available from ASKER. When urethane foam is too soft such that it has a hardness less than 10, a cosmetic composition impregnated in the urethane foam may be liberated excessively, while it is taken by cosmetic tools used for a make-up composition enclosed in a packed container, for example by nitrile butadiene rubber (NBR) puff, or hands. When urethane foam is too hard such that it has a hardness greater than 70, a cosmetic composition may not be liberated easily.

In one aspect, urethane foam may have an open cell structure. When urethane foam has a closed cell structure, air bubbles are kept in urethane so that a low-viscosity emulsion type cosmetic composition may not be impregnated therein easily. Thus, urethane foam having an open cell structure may be used specifically.

In one aspect, the cosmetic composition to be impregnated in urethane foam includes a liquid cosmetic composition, particularly an emulsion type cosmetic composition, and more particularly a water in oil (W/O) type or oil in water (O/W) type emulsion cosmetic composition.

In one aspect, the emulsion cosmetic composition may have a low viscosity, particularly of 5,000 to 15,000 centi poise (cps), and more particularly of 6,000 to 10,000 cps. When the emulsion cosmetic composition has a viscosity less than 5,000 cps, it may undergo separation into an oil phase and an aqueous phase, thereby making it difficult to impregnate urethane foam uniformly with the composition. When the emulsion cosmetic composition has a viscosity higher than 15,000 cps, it may provide an undesirably tacky and heavy touch feel while applied onto the skin.

In one aspect, the cosmetic composition includes both a skin care composition and a make-up composition. Particular non-limiting examples of the cosmetic composition may include make-up primer, make-up base, foundation, powder, twin cake, lipstick, lip gloss, eye shadow, eyebrow, concealer, lip liner, blusher, UV protecting agent, lotion, cream or essence. More particularly, the cosmetic composition may be formulated into make-up primer, make-up base, liquid or solid foundation, powder, twin cake, lipstick, lip gloss, eye shadow, eyebrow, concealer or blusher, but is not limited thereto.

Figure 2:
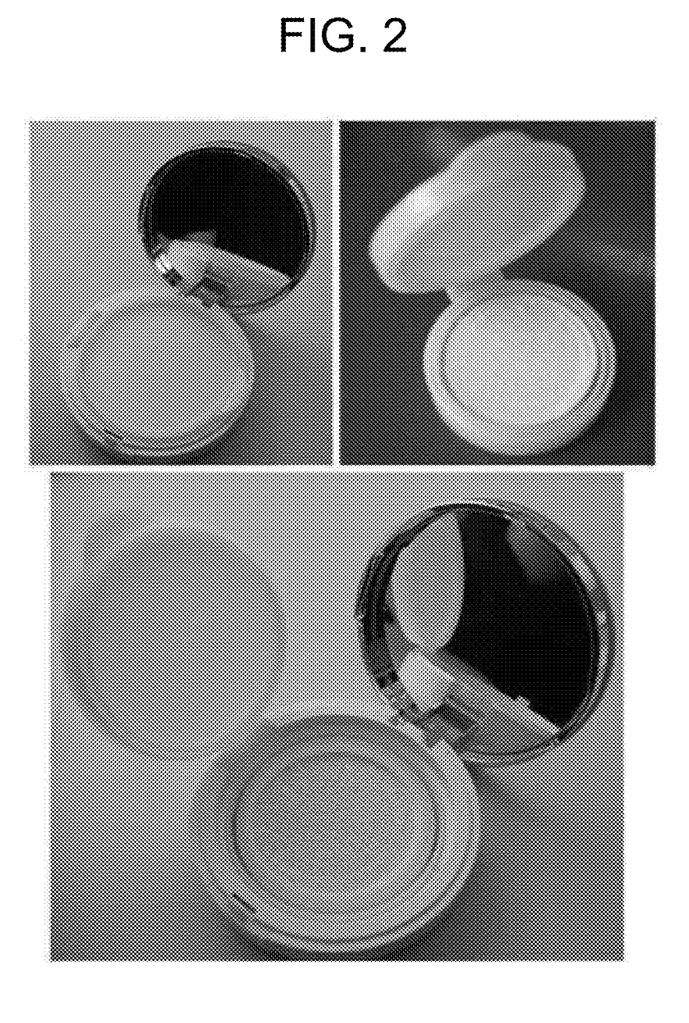
FIG. 2 shows a packed make-up product in which a urethane foam impregnated with a W/O type emulsion make-up composition is enclosed.

In one aspect, there is provided a make-up product in which polyether-based urethane foam impregnated with a cosmetic composition is enclosed. The make-up product includes a cosmetic composition applied to the polyether-based urethane foam disclosed herein, and thus allows high-quality packing of the cosmetic composition. In addition, the make-up product allows the cosmetic composition to be supported uniformly in urethane foam for a long period of time and to be liberated in an adequate amount when users take the cosmetic composition. Further, the make-up product maintains high long-term durability and stability. The make-up product disclosed herein may be provided as a packed container, abbreviated generally as 'pact', which includes a container having a lower part in which polyether-based urethane foam is received, and an upper part having a lid to which a mirror or the like may be attached. FIG. 2 shows an exemplary image of polyether-based urethane foam provided in a packed container.

The examples, comparative examples, preparation examples and test examples will now be described. The following examples are for illustrative purposes only and not intended to limit the scope of this disclosure.

[Test Example 1] Determination of Properties of Urethane Foam

Figure 3:
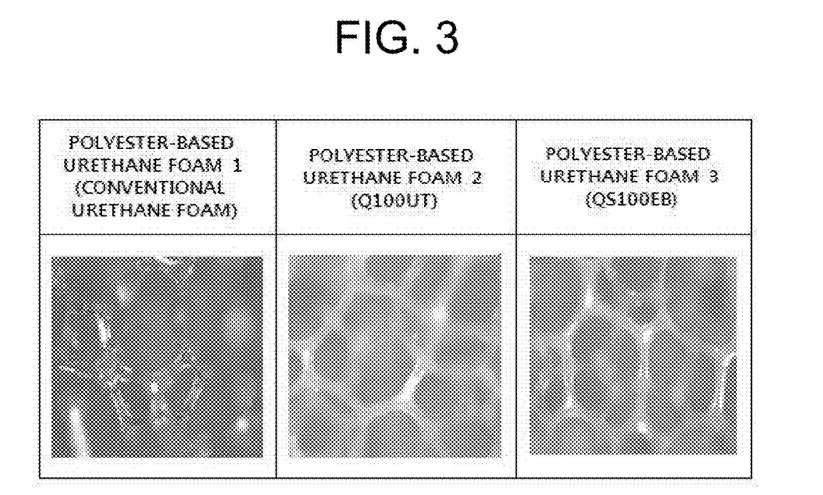
FIG. 3 is a microscopic view of the urethane foams listed in Table 2, each magnified at 10×0.3.
Figure 4:
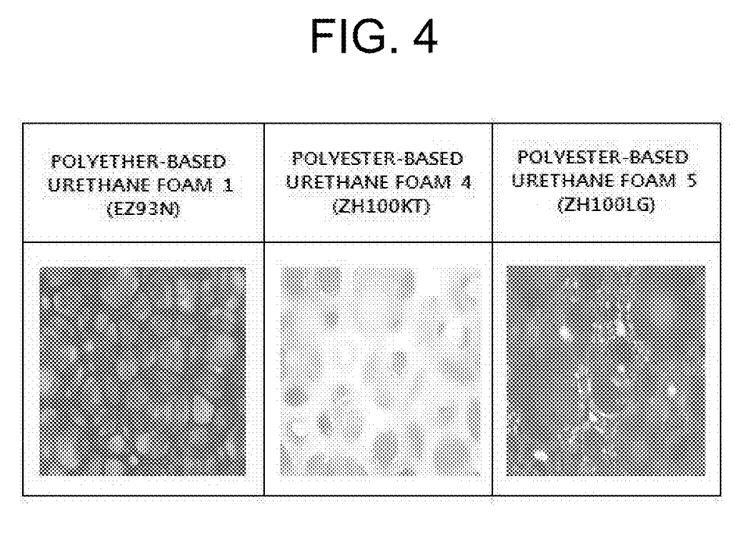
FIG. 4 is a microscopic view of the urethane foams listed in Table 3, each magnified at 10×0.3.

To select urethane foam suitable for impregnation with a W/O type or O/W type low-viscosity emulsion cosmetic composition, various types of urethane foam are determined for their properties. The following Tables 2 and 3 show each type of urethane foam and the corresponding properties. In addition, FIG. 3 and FIG. 4 are microscopic views of each type of urethane foam magnified at 10×0.3.

TABLE 2

|  | Polyester-based urethane foam 1 (conventional urethane foam) | Polyester-based urethane foam 2 (Q100UT) | Polyester-based urethane foam 3 (QS100EB) |
|---|---|---|---|
| Pore per inch (ppi) | 80 ppi | 85 ppi | 85 ppi |
| Density (pcf) |  | 1.7 | 1.7-2.0 |
| Available from | Germany | Foamtec (Thailand) | Foamtec (Thailand) |
| Remarks | Flexible polyurethane foam | Polyester-Polyurethane, Quenched foam | Polyester-Polyurethane, Reticulated foam |
| Hardness | 45 | 48 |  |

TABLE 3

|  | Polyether-based urethane foam 1 (EZ93N) | Polyester-based urethane foam 4 (ZH100KT) | Polyester-based urethane foam 5 (ZH100LG) |
|---|---|---|---|
| Pore per inch (ppi) | 88-100 ppi | 90 ppi | 90 ppi |
| Density (pcf) | 1.8-2.0 | 5.4-6.60 | 5.4-6.60 |
| Available from | Foamtec (Thailand) | Foamtec (Thailand) | Foamtec (Thailand) |
| Remarks | Polyether-Polyurethane, Reticulated foam | Polyester-Polyurethane, Reticulated foam | Polyester-Polyurethane, Reticulated foam |
| Hardness | 45 |  |  |

In Table 3, Polyether-based urethane foam 1 is dry polyether-based urethane foam.

[Test Example 2] Evaluation of Formulation Stability

Figure 5:
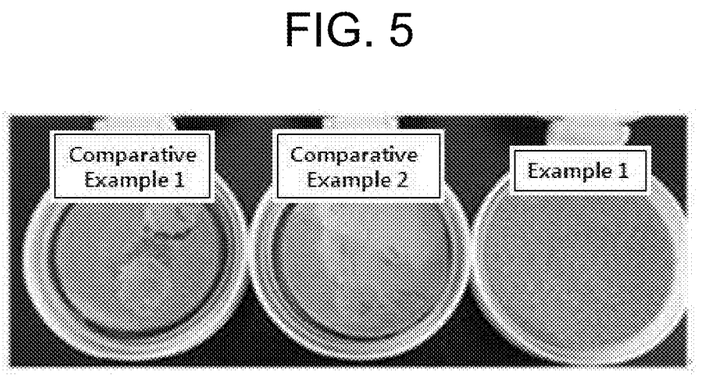
FIG. 5 shows photographs of Example 1, Comparative Example 1 and Comparative Example 2 after storing them at 50° C. for 2 hours.

Among the different kinds of urethane foam listed in Tables 2 and 3, Polyether-based urethane foam 1 (Example 1), Polyester-based urethane foam 2 (Comparative Example 1) and Polyester-based urethane foam 3 (Comparative Example 2) are selected and subjected to impregnation with a W/O type emulsion make-up composition. Then, their stabilities are evaluated as a function of storage temperature and time. The results are shown in the following Table 4 and FIG. 5. FIG. 5 shows photographs of Example 1, Comparative Example 1 and Comparative Example 2 after storing them at 50° C. for 2 hours.

TABLE 4

|  | 55° C., after 7 days | 45° C.→30° C.→ frozen at −10° C. (each for 8 hours), after 5 days | 30° C., after 7 days |
| --- | --- | --- | --- |
| Example 1 | Stable | Stable | Stable |
| Comparative Example 1 | Urethane foam broken | Urethane foam broken | Stable |
| Comparative Example 2 | Urethane foam broken | Urethane foam broken | Stable |

As can be seen from the above results, when each foam is impregnated with a W/O type emulsion make-up composition, each urethane foam according to Comparative Examples 1 and 2 is broken, causes separation of the make-up composition and generates air bubbles with time under a high temperature or severe change in temperature, and thus is shown to be very unstable. On the contrary, Example 1 substantially maintains its original state and shows high stability.

Therefore, it can be seen that polyether-urethane foam shows higher stability than polyester-based urethane foam upon impregnation with a cosmetic composition, and thus is more suitable for impregnating a cosmetic composition.

[Preparation Examples 1 and 2] Preparation of UV Protecting Cosmetic Composition In Preparation Examples 1 and 2, W/O type emulsion UV protecting cosmetic compositions are prepared according to the formulation of the following Table 5.

Particularly, a UV protecting agent is introduced to oily ingredients and dissolved and emulsified therein. Next, the oily ingredients are mixed with a surfactant and heated to and agitated at 80° C. so that the mixture is homogenized. Then, a pigment is further added thereto, followed by agitation and homogenization, to provide an oily part. In a separate mixer, aqueous ingredients are mixed and heated to and agitated at 80° C. to provide a completely dissolved aqueous part. The prepared aqueous part is introduced gradually to the oily part and subjected to emulsification by using a homogenizer mixer. After cooling to 50° C., skin protecting ingredients and fragrances are introduced thereto, followed by cooling, to provide a low-viscosity W/O type emulsion UV protecting cosmetic composition.

TABLE 5

|  |  | Ingredients (wt %) | Prep. Ex. 1 | Prep. Ex. 2 |
| --- | --- | --- | --- | --- |
| Oily Part | Oily Ingredients | Ozokerite | 0.1 | 1.0 |
|  |  | Dicaprylyl carbonate | 10.00 | 10.00 |
|  | Preservative | Methyl paraben | 0.100 | 0.100 |
|  | UV protecting agents | Octylmethoxy cinnamate | 7.000 | 7.000 |
|  |  | Isoamyl p-methoxy cinnamate | 2.000 | 2.000 |
|  | Pigment | Disteardimonium hectorite | 0.20 | 1.50 |
|  | Oily Ingredients | Decamethylcyclopentasilxane | 16.00 | 16.00 |
|  | Emulsifiers | Sorbitan sesquioleate | 2.000 | 2.000 |
|  |  | Lauryl PEG/PPG-18/18 methicon | 1.500 | 1.500 |
|  | Pigments | Polymethyl methacrylate | 5.00 | 5.00 |
|  |  | Titanium dioxide/Aluminum hydroxide/Stearic acid | 7.00 | 7.00 |
| Aq. Part |  | Water | To 100 | To 100 |
|  | Moisturizer | Glycerin | 8.000 | 8.000 |
|  | Emulsion stabilizer | Sodium chloride | 1.00 | 1.00 |
|  |  | Fragrance | 0.400 | 0.400 |
|  |  | Total | 100 | 100 |

In Table 5, disteardimonium hectorite functions as a thickening agent, polymethyl methacrylate serves as a pure body pigment, and titanium dioxide/aluminum hydroxide/stearic acid serves as an inorganic UV protecting agent.

[Test Example 3] Evaluation of Preference Depending on Hardness of Urethane Foam Different types of polyether-based urethane foam having a different value of hardness are impregnated with Preparation Examples 1 and 2, and user preference of each case is determined. Particularly, 50 females are divided into two groups (each group having 25 persons). They are allowed to apply each of Preparation Example 1 and Preparation Example 2 impregnated in polyether-based urethane foam having a different value of hardness to their skin with NBR puff for 2 days. Then, overall user preference including touch feel and coating quality is evaluated in each case. The results are shown in the following Tables 6 and 7.

TABLE 6

|  | Cosmetic composition used for impregnation | Hardness of urethane foam (ASKER hardness, Type F) | Preference (%) |
| --- | --- | --- | --- |
| Example 2 | Preparation Example 1 | 5 | 5 |
| Example 3 | Preparation Example 1 | 80 | 10 |
| Example 4 | Preparation Example 1 | 40 | 85 |

TABLE 7

|  | Cosmetic composition used for impregnation | Hardness of urethane foam (ASKER hardness, Type F) | Preference (%) |
| --- | --- | --- | --- |
| Example 5 | Preparation Example 2 | 5 | 5 |
| Example 6 | Preparation Example 2 | 80 | 5 |
| Example 7 | Preparation Example 2 | 40 | 90 |

As can be seen from the above results, the highest preference is available when polyether-based urethane foam used for impregnation with both compositions according to Preparation Examples 1 and 2 has Asker hardness value of 40.

Those skilled in the art will appreciate that the conceptions and specific embodiments disclosed in the foregoing description may be readily utilized as a basis for modifying or designing other embodiments for carrying out the same purposes of the present disclosure. Those skilled in the art will also appreciate that such equivalent embodiments do not depart from the spirit and scope of the disclosure as set forth in the appended claims.

What is claimed is:

1. A cosmetic comprising:
   a cosmetic composition; and
   a polyether-based urethane foam impregnated with the cosmetic composition;
   wherein the polyether-based urethane foam has a reticulated structure,
   wherein the cosmetic composition is taken with a cosmetic tool,
   wherein the polyether-based urethane foam is not broken when the polyether-based urethane foam impregnated with a W/O type emulsified cosmetic composition is stored at 55° C. for 7 days,
   wherein the density of the polyether-based urethane foam is 1-3 pcf (pounds per cubic feet) before the cosmetic composition is impregnated, and
   wherein the polyether-based urethane foam has a pore number of 70-120 ppi (number of pores per inch) before the cosmetic composition is impregnated.

2. The cosmetic according to claim 1, wherein the polyether-based urethane foam has a hardness of 10-70 as determined by a durometer before the cosmetic composition is impregnated.

3. The cosmetic according to claim 1, wherein the emulsified cosmetic composition has a viscosity of 5000-15000 cps.

4. The cosmetic according to claim 1, wherein the cosmetic composition is make-up primer, make-up base, foundation, powder, twin cake, lipstick, lip gloss, eye shadow, eyebrow, concealer, lip liner, blusher, UV protecting agent, lotion, cream or essence.

* * * * *